US006814616B2

(12) United States Patent
Pade

(10) Patent No.: US 6,814,616 B2
(45) Date of Patent: Nov. 9, 2004

(54) COMPACT COUPLER PLUG, PARTICULARLY FOR A PLANAR BROADBAND LAMBDA PROBE, THAT IS PROTECTED FROM DUST WHEN IN A PRE-LOCKING POSITION

(75) Inventor: Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/311,947

(22) PCT Filed: Apr. 11, 2002

(86) PCT No.: PCT/DE02/01353

§ 371 (c)(1),
(2), (4) Date: Mar. 14, 2003

(87) PCT Pub. No.: WO02/087026

PCT Pub. Date: Oct. 31, 2002

(65) Prior Publication Data

US 2003/0162440 A1 Aug. 28, 2003

(30) Foreign Application Priority Data

Apr. 19, 2001 (DE) .......................................... 201 06 747

(51) Int. Cl.[7] .............................................. H01R 13/40
(52) U.S. Cl. ........................ 439/587; 439/620; 439/587
(58) Field of Search ................................ 439/587, 620, 439/713, 76.1, 752, 588, 589, 79, 59

(56) References Cited

U.S. PATENT DOCUMENTS 6,045,403 A * 4/2000 Werner et al. .............. 439/587
6,132,256 A    10/2000 Schimansky et al.
6,146,198 A    11/2000 Maeda
6,217,394 B1    4/2001 Sugie
6,554,649 B2 * 4/2003 Pade .......................... 439/620
6,636,051 B2 * 10/2003 Pade .......................... 324/538

FOREIGN PATENT DOCUMENTS

EP          0674361 A2 * 9/1995 ......... H01R/13/533

* cited by examiner

Primary Examiner—Gary Paumen
Assistant Examiner—Edwin A. Leon
(74) Attorney, Agent, or Firm—Kenyon & Kenyon

(57) ABSTRACT

A coupler plug, configured for a planar lambda probe, for example, is described as including a housing having a base element and a cover element, as well as including electrical components configured to be inserted arid fixed in the housing, and an adjusting element for a probe, such as, for example, a planar broadband lambda probe, which is mounted in the coupler plug or outside the coupler plug, via a further contact element. The cover element is attachable over the adjusting element and includes a primary locking mechanism for arranging the cover element in a first latching position and a secondary locking mechanism for arranging the cover element in a final position, which cooperates with the cover element. To seal off the housing, at least from dirt and dust in either the first or final latching positions, a seal is mounted on the cover element, the seal having sealing lips that point away from the cover element and bring about a sealing connection with the housing in the first latching position of the cover element.

7 Claims, 3 Drawing Sheets

COMPACT COUPLER PLUG, PARTICULARLY FOR A PLANAR BROADBAND LAMBDA PROBE, THAT IS PROTECTED FROM DUST WHEN IN A PRE-LOCKING POSITION

FIELD OF THE INVENTION

The present invention relates to a coupler plug, in particular for a planar lambda probe, made up of a housing, namely a base element and a cover element, as well as electrical components, that may be inserted and fixed in the housing, and an adjusting element for a probe, such as, for example, a planar broadband lambda probe, which is mounted in the coupler plug or outside the coupler plug via a further contact element, the cover element being attachable over the adjusting element and having a primary locking mechanism (first latching position) and a secondary locking mechanism (final position) cooperating with the cover element.

BACKGROUND INFORMATION

Coupler plugs of the aforementioned type may be configured for the connection between a cable harness plug and a lambda probe, the connections in the coupler plug being provided for adjustment, signal, and/or heating of the probe. The lambda probe and the lambda control, in connection with three-way catalytic converters, may represent an effective method for cleaning exhaust emissions. The lambda probe, which, for example, may be inserted into an exhaust system, may include a sensor for determining the oxygen content in the exhaust gas.

The residual oxygen content may be well-suited for use as a measured quantity, and it may regulate the air-fuel ratio, because it may indicate precisely whether the air-fuel mixture is being completely combusted.

In this context, the lambda probe may supply a voltage signal, which represents the momentary value of the mixture composition and which may follow the mixture changes. The fuel supply to the engine may be controlled by a carburation system in accordance with the signal from the lambda probe so that a stoichiometric air-fuel ratio $\lambda=1$ is achieved. Heated or unheated probes may be used in accordance with the configuration of the exhaust gas system and the conditions in which they are used. Outside the field of motor vehicles, other applications of the lambda probe may include, e.g., regulating gas motors or oil/gas burners.

In particular, broadband lambda probes may be configured in modular form and, in combination with planar technology, may facilitate the integration of a plurality of functions. They may have functional layers, which are made up of a porous protective layer, an external electrode, a sensor film, an internal electrode, a reference gas channel film, an insulation layer, a heating element, a heating film, a resistor or adjusting element, and connection contacts.

Because broadband lambda probes may be made up of the combination of a nernet concentration cell (=sensor cell) and a pump cell that transports oxygen ions, it may measure very precisely, not only in the stoichiometric point at $\lambda=1$, but also in the lean and rich mixture ranges.

Every probe may be required to be individually adjusted. For this purpose, the probe may have a built-in resistor ("mini-hybrid"). The adjustment, which may be performed using a laser beam, may be made by properly ablating the resistance layer made up of a ceramic substrate, thereby inducing a change in the resistance, so that an adjustment follows.

One exemplary embodiment may provide for the adjustment unit, i.e., the resistor, to be mounted directly at the probe. A further exemplary embodiment may provide for the resistor to be accommodated externally, for example, on a cable harness plug that is coupled to the probe.

Heretofore, the adjustment may have been performed by transporting the housing of the coupler plug, in which the resistor is embedded, to the adjustment station without the cover element. After the appropriate laser processing for the adjustment, the cover element was mounted at a further assembly station.

To prevent the ingress of humidity, contamination or the like into the coupler plug, and to assure that the appropriate atmosphere prevails within the coupler plug, the cover element may have additional seals. Furthermore, pressure equalizer elements may be mounted on the housing of the coupler plug.

However, the seals may accomplish their sealing function only if the cover element is latched in its final position (secondary locking mechanism). When the coupler plug is transported to the adjusting station, either the cover element is completely removed, or it rests on the housing of the coupler plug, thus not accomplishing any latching function with the housing, because the cover element may be required once again to be removed in order to adjust the adjusting element. Therefore, a danger may exist, such as, for example, when the coupler plug is being transported, that dust, dirt, or humidity may penetrate into the housing, thereby impairing the functioning of the coupler plug.

SUMMARY OF THE INVENTION

The present invention may refine an embodiment of the coupler plug, such as, for example, a planar broadband lambda probe, so that the probe may be manufactured in a cost-effective manner, and, as a result of the refinement, undesired features of the related art may be avoided.

A seal may be provided on the cover element, the seal having sealing lips pointing away from the cover element, the sealing lips, in the first latching position of the cover element, bringing about a sealing connection with the housing.

The coupler plug may be configured to be of small construction, because, due to the compact configuration, i.e., the insertion of electrical contacts into a base element and the placement of the adjusting element likewise in the coupler plug, the exterior dimensions of the coupler plug, which may be positioned between a cable harness and a lambda probe, may be small.

In addition, an exemplary coupler plug according to the present invention may have only a small number of components. As a result, a cost-effective and efficient manufacturing process may be provided.

Because the base element is completely enclosed by the cover element, the interior of the coupler plug may be sealed off by configuring the sealing lips within the cover element, thereby protecting it, for example, from dust, dirt, or water spray, even in the first latching position of the cover element.

In addition, this may also support the latching of the cover element to the base element. A first and a second latching mechanism, i.e., a primary and secondary locking mechanism, may be provided. The latter may be configured such that the cover element has latching arms, which, in the closed state of the cover, contact the base element of the coupler plug and produce a latching there using detents. In the first latching position, the sealing lips mounted on the circumferential seal on the cover element already engage in cutouts on the sides of the housing and therefore may provide protection at least against dust and dirt. By once again pressing the cover element in the direction of the housing, the circumferential seal that is mounted in the cover element may become functional when the final position (the secondary locking mechanism) is reached, and it may completely seal the housing from its external environment. The seal may be configured so that the housing is watertight in the final position of the cover element. In this final position, the sealing lips may cease functioning and may all but completely accommodated in the cutout in the housing.

The aforementioned seal may be injection-molded on the cover element, so that it is non-detachably mounted.

The cover element may be made of PBT (polybutylene terephthalt) or a similar material.

DETAILED DESCRIPTION

Figure 1:
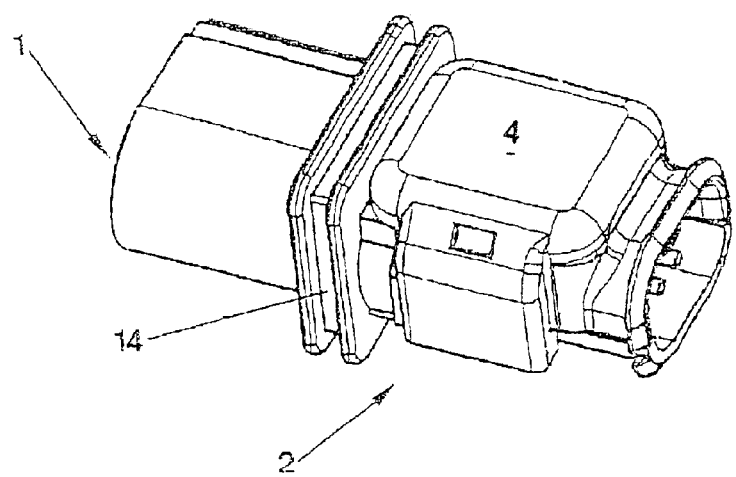
FIG. 1 shows a perspective view of an exemplary coupler plug according to the present invention, having a cover element in the final position.
Figure 2:
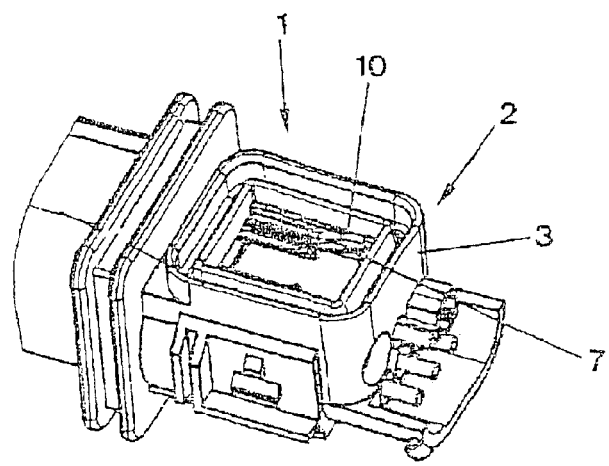
FIG. 2 shows a perspective view of the exemplary coupler plug according to the present invention, without the cover element.
Figure 3:
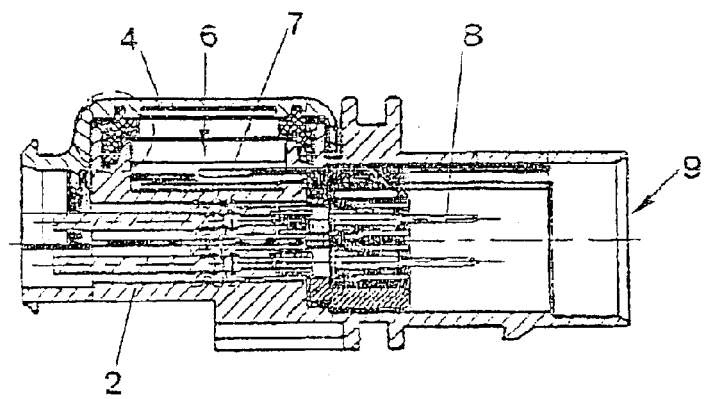
FIG. 3 shows a longitudinal cutaway view of the exemplary coupler plug according to FIG. 1.
Figure 4:
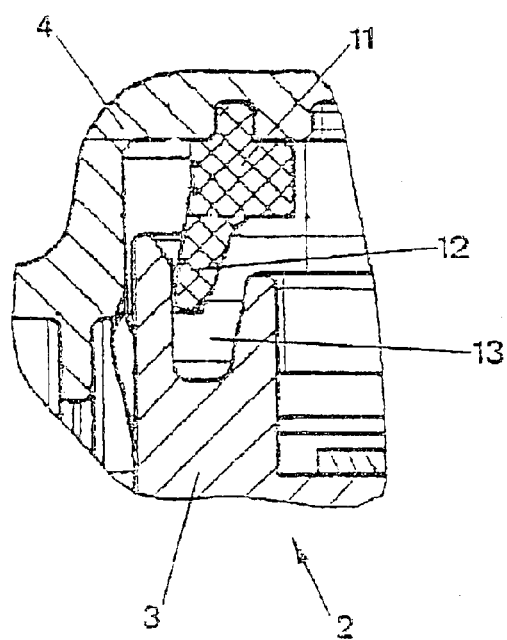
FIG. 4 shows a detail representation of FIG. 3, the functioning of the cover element together with the seal and sealing lips being depicted in a cutaway view, and the cover element being arranged in a first latching position.

Coupler plug 1, depicted in FIGS. 1 through 5, is a type of plug that is made up of a housing 2, which is composed of a base element 3 and a cover element 4.

On base element 3, an adjustment unit 6 is mounted in a holding device 5, the adjustment unit in turn being connected via electrical contact elements 7 to the lambda probe that is connected via a connecting element 8, or to the plug that is inserted into coupler plug 1 and is not depicted in greater detail in the drawings.

Electrical contact elements 7 are made up of metal strips that are shaped like printed circuit traces, which in the area of coupling potential 9 (FIG. 4) of coupler plug 1 terminate in their one side.

Adjustment unit 6 is guided by guide elements 10, that are mostly configured on base element 3, and the adjustment unit is held in position by electrical contact elements 7.

Cover element 4 on its interior side has a circumferential seal 11, which, in the assembled state of cover element 4, corresponds to the housing. In addition, sealing lips 12 are mounted on seal 11 so as to point away from cover element 4. These sealing lips 12 taper towards their ends. The length of sealing lips 12 is dimensioned such that, when cover element 4 is placed on housing 2 in the first latching position, depicted in FIG. 4, they extend into cutout 13, so that housing 2 is sealed off.

Figure 5:
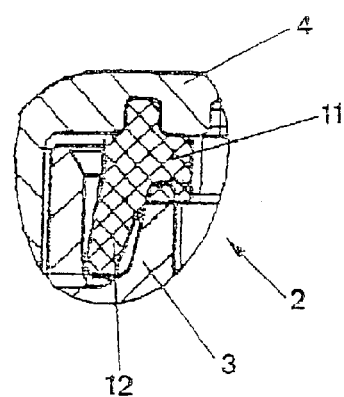
FIG. 5 shows a detail representation of FIG. 3, the functioning of the cover element together with the seal and sealing lips being depicted in a cutaway view, and the cover element being arranged in a final position.

By bringing about the final position of cover element 4, as depicted in FIG. 5, the result is that sealing lips 12 are pressed further into cutouts 13, and the actual seal between circumferential seal 11 and housing 2 is accomplished.

Seal 11 and sealing lips 12 may constitute a single piece and may be injection-molded non-detachably on the interior side of cover element 4.

Coupler plug 1 on its periphery may have grooves 14, which may permit a coupler plug 1 to be inserted in holders that are provided for this purpose.

Due to its small exterior dimensions, the coupler plug may be accommodated in a grooved tube.

What is claimed is:

1. A coupler plug, comprising:

a first contact element;

a probe mounted one of in the coupler plug and outside the coupler plug via the first contact element;

an adjusting element for the probe;

a housing including a base element and a cover element, the cover element being attachable over the adjusting element and including a primary locking mechanism for arranging the cover element in a first latching position and a secondary locking mechanism for arranging the cover element in a final position, which cooperates with the cover element;

a plurality of electrical components configured to be inserted and fixed in the housing; and a seal arranged on the cover element and having sealing lips that point away from the cover element, the sealing lips configured to bring about a sealing connection with the housing in the first latching position of the cover element;

wherein a cutout is arranged in the housing so that, in the first latching position of the cover element, the sealing lips penetrate into the cutout and lean against a wall of the cutout to seal off the housing; and wherein, in the final position of the cover element, the sealing lips are all but completely engaged in the cutout provided in the housing, and the seal completely seals off the housing.

2. The coupler plug according to claim 1, wherein the coupler plug is configured for a planar lambda probe.

3. The coupler plug according to claim 1, wherein the probe includes a planar lambda probe.

4. The coupler plug according to claim 1, wherein the sealing lips along with a remaining portion of the seal constitute a single piece.

5. The coupler plug according to claim 1, wherein the seal and the sealing lips are made of different materials.

6. The coupler plug according to claim 1, wherein the seal is fixedly joined to the cover element.

7. The coupler plug according to claim 6, wherein the seal is injection-molded onto the cover element.

* * * * *